(12) United States Patent
Liang

(10) Patent No.: US 11,402,277 B2
(45) Date of Patent: Aug. 2, 2022

(54) TEMPERATURE MEASURING DEVICE ADOPTING A PLURALITY OF INFRARED SENSORS AND ITS METHOD

(71) Applicant: Cao Liang, Guangdong (CN)

(72) Inventor: Cao Liang, Guangdong (CN)

( * ) Notice: Subject to any disclaimer, the term of this patent is extended or adjusted under 35 U.S.C. 154(b) by 878 days.

(21) Appl. No.: 16/242,819

(22) Filed: Jan. 8, 2019

(65) Prior Publication Data
US 2019/0212214 A1    Jul. 11, 2019

(30) Foreign Application Priority Data

Jan. 8, 2018  (CN) .......................... 201810014007.7

(51) Int. Cl.
| | | |
|---|---|---|
| *G01J 5/00* | (2022.01) | |
| *G01K 13/20* | (2021.01) | |
| *A61B 5/01* | (2006.01) | |
| *A61B 5/00* | (2006.01) | |
| *G01J 5/02* | (2022.01) | |
| *G01J 5/07* | (2022.01) | |
| *G01J 5/0802* | (2022.01) | |
| *G01J 5/80* | (2022.01) | |

(52) U.S. Cl.
CPC .......... *G01K 13/223* (2021.01); *A61B 5/0059* (2013.01); *A61B 5/0075* (2013.01); *A61B 5/01* (2013.01); *A61B 5/6844* (2013.01); *G01J 5/0025* (2013.01); *G01J 5/026* (2013.01); *G01J 5/0275* (2013.01); *G01J 5/07* (2022.01); *G01J 5/0802* (2022.01); *G01J 5/80* (2022.01); *A61B 2562/0271* (2013.01); *A61B 2562/04* (2013.01); *G01J 2005/0092* (2013.01)

(58) Field of Classification Search
CPC combination set(s) only.
See application file for complete search history.

(56) References Cited

U.S. PATENT DOCUMENTS

| | | | | |
|---|---|---|---|---|
| 6,898,457 B1 * | 5/2005 | Kraus | .................... | G01J 5/0806 600/549 |
| 2010/0041998 A1 * | 2/2010 | Postel | .................... | A61B 5/015 600/475 |

(Continued)

FOREIGN PATENT DOCUMENTS

| | | | | |
|---|---|---|---|---|
| WO | WO-2011151806 A1 * | 12/2011 | ............... | A61B 5/01 |
| WO | WO-2014149976 A1 * | 9/2014 | ............ | G01J 5/0265 |

*Primary Examiner* — Lisa M Caputo
*Assistant Examiner* — Nasir U. Ahmed
(74) *Attorney, Agent, or Firm* — Rumit Ranjit Kanakia

(57) ABSTRACT

The invention discloses a temperature measuring device adopting a plurality of infrared sensors and its method. The temperature measuring device consists of a housing, a main control circuit board unit set in the housing, a power supply unit and an infrared sensor set at the head of the housing, wherein the main control circuit board unit is a main control circuit board, and a main control Microcontroller Unit, a signal acquisition circuit, a display screen, a power supply and a control key integrated in the main control circuit board. The method is to calculate and output the accurate target temperature through infrared sensors combined with Microcontroller Unit, at the same time, it can effectively identify such as abnormality of measurement area, abnormality of user measurement method and so as to improve the effectiveness of measurement results.

8 Claims, 11 Drawing Sheets

(56) References Cited

U.S. PATENT DOCUMENTS

| | | | |
|---|---|---|---|
| 2012/0075463 A1* | 3/2012 | Chen | G01S 11/12 |
| | | | 348/E5.09 |
| 2013/0116573 A1* | 5/2013 | Herman | A61B 5/444 |
| | | | 600/474 |
| 2015/0120360 A1* | 4/2015 | Adriaenssens | G01V 8/10 |
| | | | 705/7.16 |
| 2015/0265159 A1* | 9/2015 | Lane | A61B 5/0077 |
| | | | 600/549 |
| 2016/0007925 A1* | 1/2016 | Mirov | G01B 11/14 |
| | | | 356/400 |
| 2016/0363483 A1* | 12/2016 | Tzvieli | G01J 5/12 |

* cited by examiner

TEMPERATURE MEASURING DEVICE ADOPTING A PLURALITY OF INFRARED SENSORS AND ITS METHOD

TECHNICAL FIELD

The invention relates to the technical field of temperature measurement, in particular to a temperature measuring device adopting a plurality of infrared sensors and its method.

BACKGROUND OF THE INVENTION

It is well known that all objects above absolute zero in nature radiate energy constantly. According to the blackbody radiation law, the size of the object's outward radiation energy and its distribution by wavelength are closely related to its surface temperature. The higher the object's temperature, the stronger the infrared radiation capacity it emits. The infrared thermometer uses the infrared receiving sensor to obtain the infrared radiation emitted by skin surface of human body, accurately measures the skin temperature of human body, and corrects the temperature difference between the forehead and actual body temperature with the aid of internal algorithm of the thermometer, so as to obtain the accurate body temperature. Because the forehead is close to the heart, the blood flow is supplied by the aorta and carotid artery through the temporal artery, and the blood circulation is fast, which can reflect the change of body temperature in time. When a fever occurs, the brain is first affected. When the body temperature rises or falls, the human body first adjusts the temperature from the brain, and the surface temperature of forehead can be quickly reflected. The infrared thermometer acquires the infrared radiation from the forehead part of human body through special infrared sensor receiving probes and can effectively obtain the body temperature through a series of algorithms.

At present, the infrared temperature guns on the market all use a single temperature sensor, and only one temperature value can be measured at a time. Due to the error of the infrared temperature gun itself, the temperature value at a time cannot accurately reflect the temperature condition at that time. In order to obtain an accurate temperature value, it is generally required to measure the temperature at the same place several times and then select a valid value, which bringing trouble and difficulty to the temperature measurement and making it inconvenient to operate. For the infrared temperature gun with a single sensor, the acquisition area is small and standardized operation is required. The difference in forehead temperature distribution among different objects cannot be eliminated, which affects the accuracy of measurement. At the same time, it can not effectively judge when various conditions such as abnormity of measurement area, incorrect measurement position or improper measurement distance occur, resulting in inaccurate measurement data and the whole device is out of use. From a medical point of view, if the real body temperature is not detected in real time for patients with high fever, it may delay the best treatment time and cause serious consequences. Therefore, it is a general trend to improve the accuracy of temperature measurement to promote the products of temperature measuring devices.

SUMMARY OF INVENTION

In order to solve the problem of accuracy deviation of temperature measurement caused by the small acquisition area of a single infrared sensor in the existing temperature measuring device; the problem of unable to judge whether there is abnormity in the acquisition area; the problem of unable to eliminate the measurement result difference caused by blood vessel distribution difference in the measurement target position; the problem of unable to identify errors in user measurement position; the problem that a single sensor can not compensate for the temperature deviation; the problem of unable to judge the effective measuring distance and inaccurate temperature measurement, and in order to improve the accuracy of temperature detection. The invention provides a temperature measuring device adopting a plurality of infrared sensors and its method.

The technical scheme of the invention is: A temperature measuring device adopting a plurality of infrared sensors, which consists of a housing, a main control circuit board unit set in the housing, a power supply unit and an infrared sensor set at the head of the housing, wherein the main control circuit board unit is a main control circuit board, and a main control Microcontroller Unit, a signal acquisition circuit, a display screen, a power supply and a control key integrated in the main control circuit board, characterized in that the infrared sensors arranged at the head of the housing include at least two infrared sensors, and all the infrared sensors are connected to a signal acquisition circuit.

All the infrared sensors mentioned are arranged side by side in parallel with the head of the housing; or partial infrared sensors and the rest of the infrared sensors are obliquely arranged, and the front ends of the two parts of infrared sensors form an included angle.

The front end of the infrared sensors mentioned is respectively provided with different types of filters to respectively acquire infrared signals in different wave bands The technical scheme discloses the temperature measuring method of a temperature measuring device adopting a plurality of infrared sensors, characterized in that the infrared sensors start to work through a signal acquisition circuit to respectively acquire the temperatures T1, T2 . . . Tn, which are then calculated and analyzed through the main control Microcontroller Unit, and main control Microcontroller Unit operation temperature value includes the following operations Target temperature: $T_{target} = (T1+T2+ \ldots Tn)/n$ The problem of uneven distribution of target temperature is eliminated by expanding the acquisition area through a plurality of sensors, and a more accurate target temperature value is obtained.

Target temperature: $T_{tag} = MAX(T1: T2: \ldots :Tn)$

Max is a function to take the maximum value

This formula is to identify the region contains blood vessels by the algorithm after acquiring a plurality of areas through a plurality of sensors, set the blood vessel region as the human body temperature, filter out other regions, and get a more accurate target temperature value.

Standard Deviation of Sample Temperature Value:

$$\Delta T = \sqrt{\frac{(T2-T1)^2 + (T3-T1)^2 + \ldots + (Tn-T1)^2}{n-1}}$$

The formula is to calculate the standard deviation by Microcontroller Unit after acquiring a plurality of areas through a plurality of sensors, and the main control Microcontroller Unit sets a threshold value $T_{threshold\ value}$, when the calculated standard deviation of temperature $\Delta T > T_{threshold\ value}$, it can be judged that there is an abnormality in the target measuring area or in the user measurement area, and the temperature measuring device sends out an error alarm prompt.

The temperature measuring method of a temperature measuring device adopting a plurality of infrared sensors, including matching different filters to infrared sensors, the main control Microcontroller Unit sets the weight values K1, K2 . . . Kn corresponding to different types of filters, and carries out weight calculation corresponding to the temperature values T1, T2 . . . Tn measured by a plurality of infrared sensors, including the following operation:

Target temperature $T_{tag} = K1*T1 + K2*T2 + \ldots + Kn*Tn$

Through the above operation of target temperature $T_{tag}$, different filters are used for the same area acquired by a plurality of infrared sensors, and a plurality of infrared sensors receive signals in different wavebands and then perform mutual compensation operation. At the same time, filters and algorithms can be used to filter externally connected interference infrared signals and improve the accuracy of temperature measurement.

The temperature measuring method of a temperature measuring device adopting a plurality of infrared sensors also includes that a plurality of infrared sensors are used for temperature measurement to realize fixed distance measurement, so as to prevent users from far measurement and realize alarm prompt for far measurement. A plurality of infrared sensors are divided into two parts, partial infrared sensors and the other part of the infrared sensors are obliquely arranged, and the front ends of the two parts of infrared sensors form an included angle and form different temperature acquisition angles, while one part of which uses a small angle of about 30 degrees for temperature measurement and the other part uses a large angle of about 60 degrees for fixed distance. The main control Microcontroller Unit then performs the following operation:

$\Delta T = MAX(|T2-T1|:|T3-T1|: \ldots :|Tn-T1|)$

Max means to take a large value, the main control Microcontroller Unit sets a threshold value $T_{threshold\ value}$, when $\Delta T > T_{threshold\ value}$, it can be judged that the measurement distance is too far, and the temperature measuring device sends out an error alarm prompt.

The technical scheme of the invention adopts a plurality of infrared sensors to realize the temperature measuring device, which has the following beneficial effects: two or more infrared sensors enlarge the signal acquisition area, eliminate the problem of uneven distribution of target temperature, and enable the acquired signals to be more accurate; Judging whether there is abnormity in the acquisition area through signal differences of signals received by a plurality of infrared sensors; Through the analysis and compensation of the input signals of a plurality of infrared sensors, the uneven skin temperature caused by the difference of blood vessel distribution in human body can be eliminated, and the blood vessel position temperature can be directly obtained to improve the accuracy of measurement; A plurality of infrared sensors can effectively identify whether the user is using correctly and improve the effectiveness of measurement; Through a plurality of infrared sensors, different filters are added to acquire infrared signals in different wave bands respectively, and then synthetic analysis of the infrared signals are conducted, at the same time, filters and algorithms can be used to filter externally connected interference infrared signals and improve the accuracy of temperature measurement; A plurality of infrared sensors can effectively identify the distance when the user uses it and improve the effectiveness of measurement.

DETAILED DESCRIPTION OF THE PREFERRED EMBODIMENT

The invention will be further described with reference to the attached diagrams and specific embodiments. The attached diagrams are examples of setting up two infrared sensors to measure the forehead position of a human body, but the following embodiments are not intended to limit the invention to designing only two infrared sensors and measuring positions.

Figure 1:
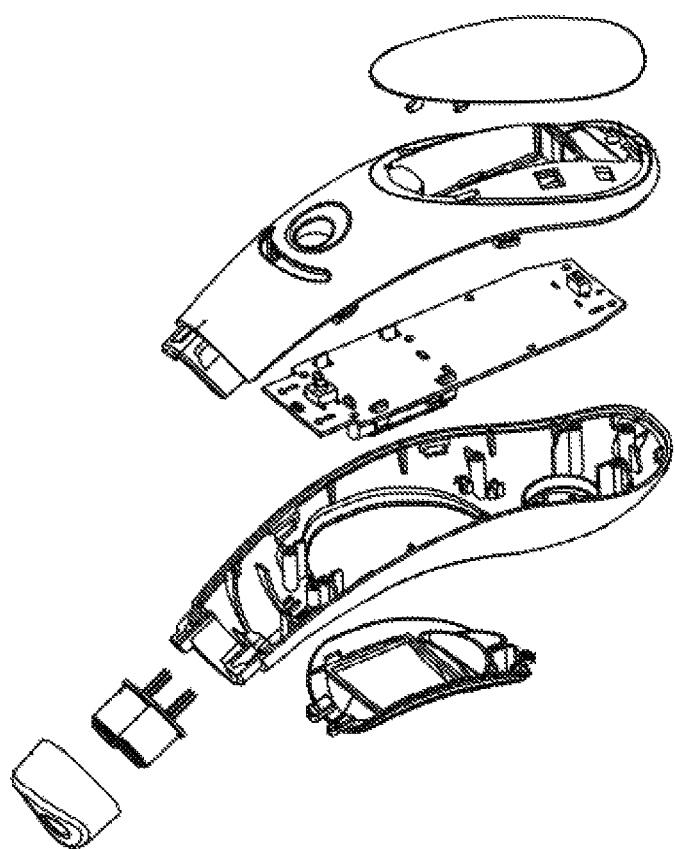
FIG. 1 is a schematic structural diagram of an embodiment in which two infrared sensors are provided.
Figure 2:
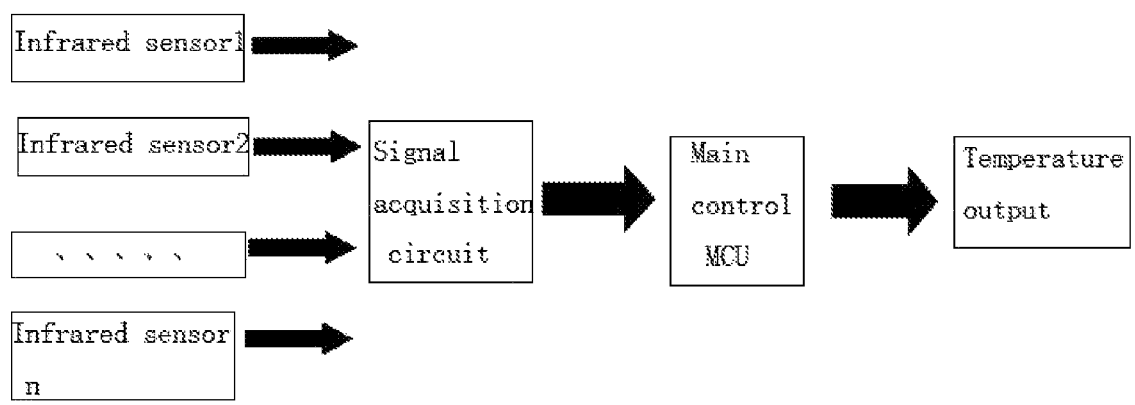
FIG. 2 is a working principle block diagram of the utility model.

According to attached FIGS. 1-2, a temperature measuring device adopting a plurality of infrared sensors, which consists of a housing, a main control circuit board unit set in the housing, a power supply unit and an infrared sensor set at the head of the housing, wherein the main control circuit board unit is a main control circuit board, and a main control Microcontroller Unit, a signal acquisition circuit, a display screen, a power supply and a control key integrated in the main control circuit board, characterized in that the infrared sensors arranged at the head of the housing include at least two infrared sensors, which are respectively an infrared sensor A and an infrared sensor B as exemplified in FIG. 1, and both the infrared sensors A and B are connected to a signal acquisition circuit.

The infrared sensors mentioned are arranged side by side in parallel with the head of the housing; or infrared sensors A and B are obliquely arranged, and the front ends of infrared sensors A and B form an included angle.

Figure 3:
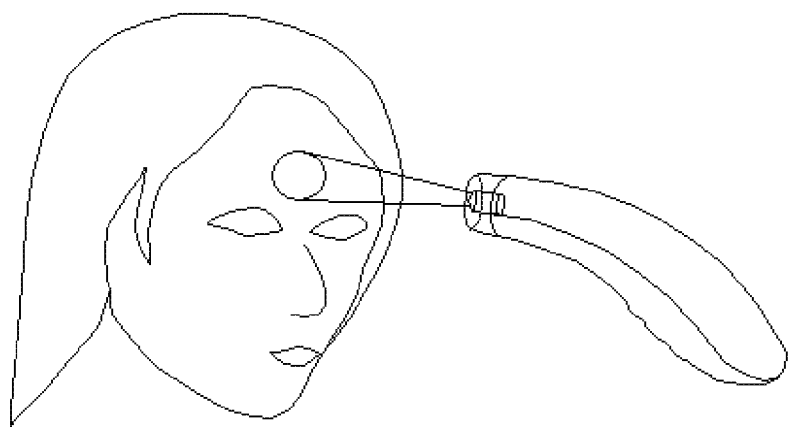
FIG. 3 is a schematic diagram for the effect of temperature measurement acquisition area of a traditional single infrared sensor.
Figure 4:
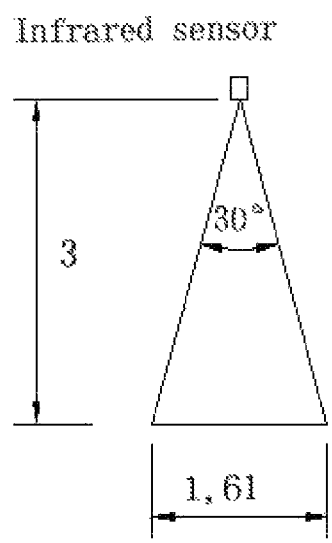
FIG. 4 is a schematic diagram for parameters of acquisition area of a single infrared sensor.
Figure 5:
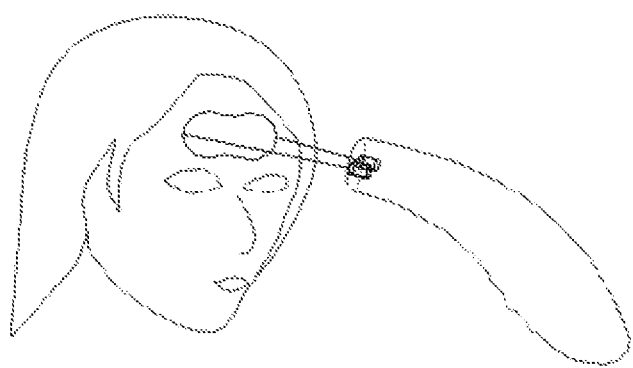
FIG. 5 is the effect diagram of temperature measurement acquisition area by using two infrared sensors of the utility models.
Figure 6:
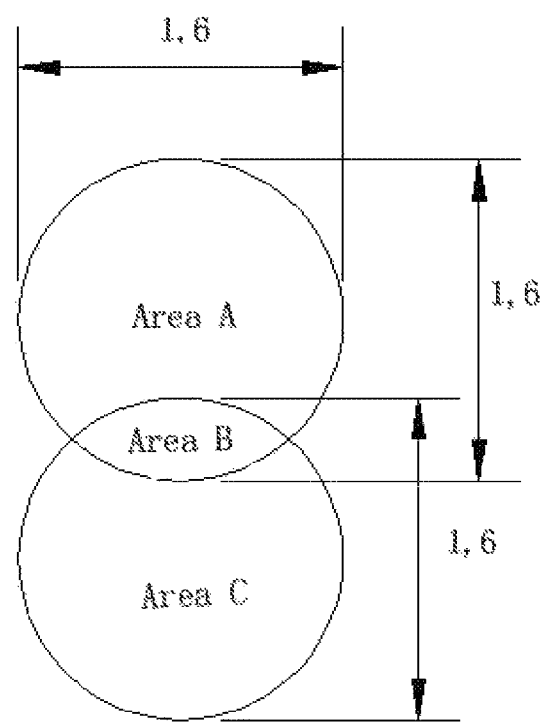
FIG. 6 is a schematic diagram for the parameters of temperature measurement acquisition area of two infrared sensors.
Figure 7:
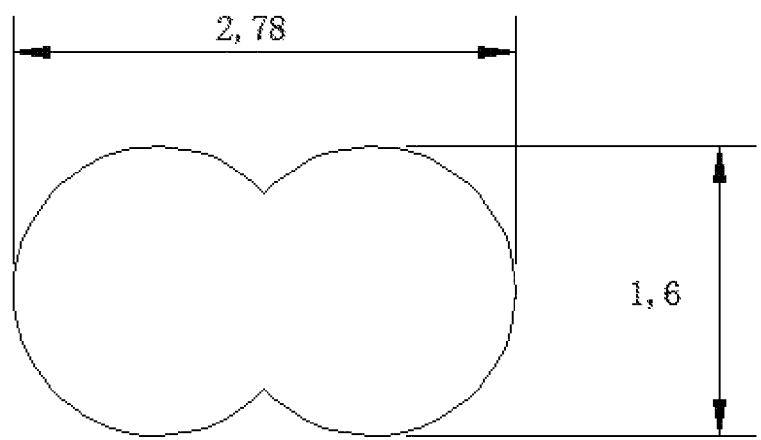
FIG. 7 is a schematic diagram for the area parameters of temperature measurement acquisition area of two infrared sensors.

According to attached FIG. 3, the traditional temperature measuring device using a single infrared sensor usually has an acquisition angle of about 30 degrees and a measurement distance of about 3 cm. FIG. 4 shows that the acquisition area is a circular area with a diameter of about 1.6 cm. FIG. 5 is the schematic diagram of temperature measurement by using two infrared sensors, it can be concluded that the acquisition temperature measurement area is obviously larger than that of a single infrared sensor. Attached FIGS. 6-7 show that the two sensors adopt the same angle and measurement distance, and the acquisition area is expanded to about 1.8 times of that of a single infrared sensor, and the acquisition area is more in line with the forehead shape.

According to the target temperature measurement operation disclosed by the invention, the target temperature includes the following two operations:

$$\text{Target temperature: } T_{target}=(T1+T2)/2$$

There are some differences in the temperature distribution of forehead of human body. Through this calculation, the difference in temperature distribution can be eliminated and the accuracy of measurement can be improved $$\text{Target temperature: } T_{tag}=\text{MAX}(T1:T2)$$

The blood vessel temperature is the closest to temperature of the human body and the epidermis temperature of blood vessel accessories is generally higher than other epidermis temperatures. However, due to the distribution of blood vessels in human head, there will be differences in the positions of blood vessels of different people. When a single sensor is used, it is not possible to judge whether blood vessels are contained, but if a plurality of sensors are used, it is possible to effectively determine which region contains blood vessels, take out the measured maximum value, select the region contains blood vessel positions and set it as the temperature value of human body, thus obtaining a more accurate measurement result.

Figure 8:
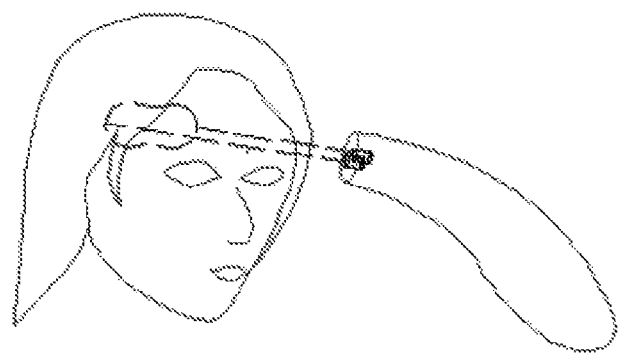
FIG. 8 is a schematic diagram for effect of abnormity in temperature measuring area.
Figure 9:
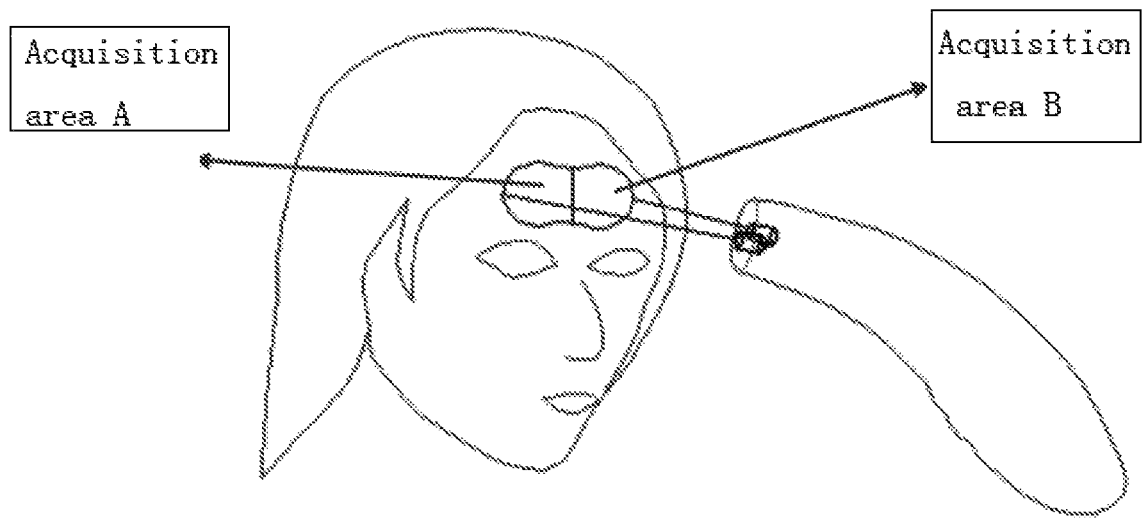
FIG. 9 is the effect diagram of temperature measurement in two areas acquired by two infrared sensors.

The measurement method disclosed in the technical scheme can accurately judge the abnormality of the measurement target position, and when various abnormal conditions such as redness, inflammation, foreign matters (such as water, sweat, cosmetics, etc.) appear on human skin, the skin problem in the abnormal area is obviously higher or lower than the skin temperature in normal area. Or there may be other barriers, as shown in FIG. 8, there may be abnormity of hair barriers at the measurement position. According to attached FIG. 9, the two infrared sensors are adopted, and acquisition areas can be divided into acquisition area A and acquisition area B, and the acquired temperatures are T1 and T2 respectively, by calculating the standard deviation of sampling values of the infrared sensors.

$$\Delta T=\sqrt{(T2-T1)^2}$$

When the calculated standard deviation of temperature $\Delta T>T_{threshold\ value}$, it can be judged that there is an abnormality in the target area, and the temperature measuring device sends out an error alarm prompt.

The front ends of the infrared sensor A and the infrared sensor B are respectively provided with different types of filters. The lower receiving limit of infrared sensor A is infrared radiation wavelength of 5-10 um, while the upper receiving limit of infrared sensor B is infrared radiation wavelength of 10-15 um.

The two sensors acquire the same area, but with different filters, the two sensors receive signals in different wave bands and then perform mutual compensation operation to improve the accuracy of measurement. The wavelength of human infrared radiation is about 10 um. According to human infrared distribution characteristics, different weights K1 and K2 are given, and then the final target temperature is calculated through the following formula.

$$\text{Target temperature } T_{tag}=K1*T1+K2*T2$$

Figure 10:
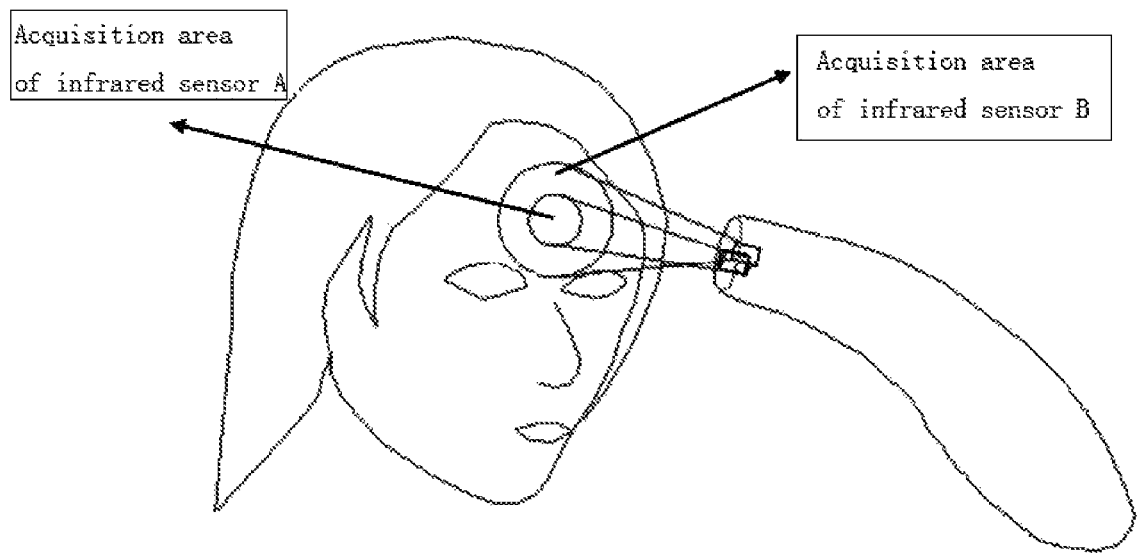
FIG. 10 is the effect diagram of temperature measurement and interval using two infrared sensors that form an included angle.
Figure 11:
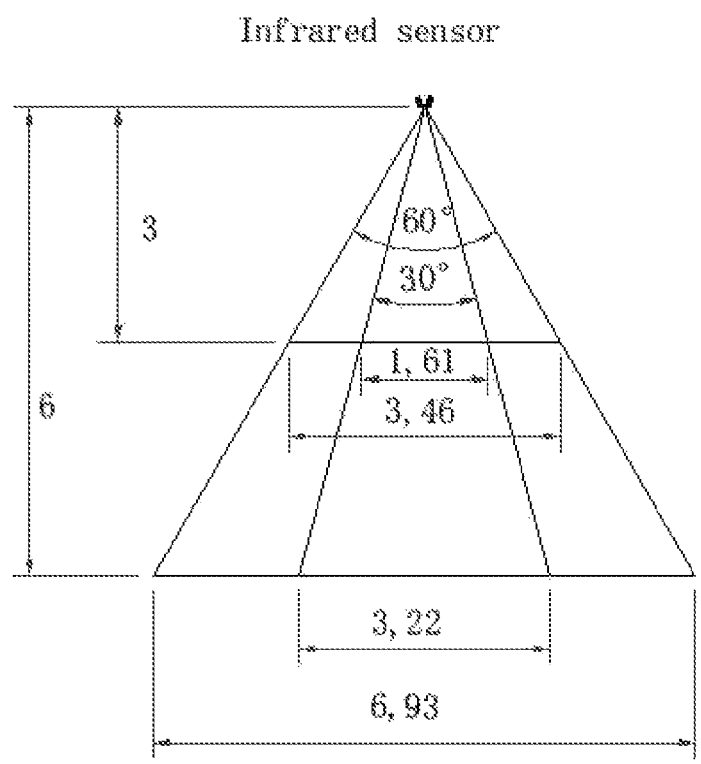
FIG. 11 is a schematic diagram for parameters of temperature measurement and interval using two infrared sensors that form an included angle.

According to attached FIG. 10, attached FIG. 11 is the interval measurement using two infrared sensors. Infrared sensors A and B are obliquely arranged, and the front ends of infrared sensors A and B form an included angle.

The effective temperature measurement area on the forehead of a normal person is a circle with a diameter of about 4 cm, and measurement beyond this range will lead to inaccurate temperature measurement. According to attached FIG. 10 and FIG. 11, the infrared sensor A and infrared sensor B are designed with different acquisition angles, wherein the optical path of infrared sensor A is designed to have a small angle of about 30 degrees, mainly used for temperature measurement, and the acquisition optical angle of another infrared sensor B is designed to have a large angle of about 60 degrees, mainly used for distance. As can be seen from FIG. 11, when the measuring distance is about 3 cm, the largest acquisition area of the two is a circle with a diameter of about 3.46 cm, which is within the acceptable range; However, when the measuring distance is about 6 cm, the acquisition range of the infrared sensor for temperature measurement is a circle with a diameter of about 3.22 cm and can measure the temperature normally, but the acquisition diameter of the infrared sensor for distance becomes 6.93 cm and can not measure the temperature correctly, $\Delta T=\text{MAX}(|T2-T1|)$, when $\Delta T>T_{threshold}$, we judge that the measuring distance is too far, then the temperature measuring device sends out an error alarm prompt, thus adjusting the measuring distance.

The above embodiments of the invention are merely examples for clearly illustrating the invention and are not intended to limit the embodiments of the invention. However, obvious changes or variations which are derived from the essential spirit of the invention still belong to the protection scope of the invention.

The invention claimed is:

1. A temperature measuring device having a plurality of infrared sensors, comprising:
    a housing;
    a main control circuit board unit set in the housing; and
    the plurality of infrared sensors set at a head of the housing, wherein one part of the plurality of infrared sensors and the other part of the plurality of infrared sensors are obliquely arranged, and the front ends of the one part and the other part form an angle;
    wherein the main control circuit board unit comprises a main control circuit board, and a main control Microcontroller Unit, a signal acquisition circuit, a display screen, a power supply and a control key integrated on the main control circuit board, wherein the plurality of infrared sensors arranged at the head of the housing include at least two infrared sensors, at least two infrared sensors are connected to the signal acquisition circuit, and the main control Microcontroller Unit is configured to identify an abnormality of temperature measurement area, an abnormality of temperature measurement distance and to output an accurate target temperature.

2. The temperature measuring device having a plurality of infrared sensors as defined in claim 1, wherein front ends of the plurality of infrared sensors are respectively provided with different types of filters to respectively acquire infrared signals in different wave bands.

3. A temperature measuring method using a temperature measuring device having a plurality of infrared sensors wherein the temperature measuring device comprises a main control circuit board, and a main control Microcontroller Unit, a signal acquisition circuit, a display screen, a power supply and a control key integrated on the main control circuit board, wherein one part of the plurality of infrared sensors and the other part of the plurality of infrared sensors are obliquely arranged, and the front ends of the one part and the other part form an included angle, the method comprising:
   controlling the infrared sensors to start to work through the signal acquisition circuit;
   acquiring temperatures T1, T2 . . . Tn;
   determining a target temperature based on the temperatures T1, T2 . . . Tn.

4. The temperature measuring method according to claim 3, wherein the acquiring comprises: acquiring temperatures T1, T2 . . . Tn at a plurality of areas from the plurality of infrared sensors, wherein the plurality of areas comprises a region where blood vessels are located; and
   Wherein the determining comprises: determining a target temperature to be a maximum value of the temperatures T1, T2 . . . Tn:
   Target temperature: $T_{tag}=MAX(T1:T2: \ldots :Tn)$.

5. The temperature measuring method according to claim 3, wherein the plurality of infrared sensors are equipped with different filters respectively, the determining comprises:
   determining a target temperature based on weight values K1, K2 . . . Kn corresponding to the different types of filters and the temperature values T1, T2. . . Tn:
   Target temperature $T_{tag}=K1*T1+K2*T2+ \ldots +Kn*Tn$.

6. The temperature measuring method according to claim 3, further comprising:
   performing a standard deviation calculation through the main control Microcontroller Unit:

$$\Delta T = \sqrt{\frac{(T2-T1)^2+(T3-T1)^2+\ldots+(Tn-T1)^2}{n-1}},$$

the main control Microcontroller Unit sets a threshold value $T_{threshold\ value}$, when $\Delta T > T_{threshold\ value}$, it can effectively judge that the user's target area is abnormal or the user's measurement position is wrong.

7. The temperature measuring method according to claim 3, wherein the one part of the plurality of infrared sensor uses a small angle of 30 degrees for temperature measurement and the other part uses a large angle of 60 degrees for distance measurement, the method further comprising: performing following calculation:

$$\Delta T=MAX(|T2-T1|:|T3-T1|: \ldots :|Tn-T1|)$$

Max means to take a large value, the main control Microcontroller Unit sets a threshold value $T_{threshold\ value}$, when $\Delta T > T_{threshold\ value}$, it can be judged that the measurement distance is too far, and the temperature measuring device sends out an error alarm prompt.

8. The temperature measuring method according to claim 3, wherein the target temperature is determined to be an average of the temperatures T1, T2 . . . Tn by the main control Microcontroller Unit: $T_{target}=(T1+T2+ \ldots Tn)/n$.

* * * * *